(12) United States Patent
Haanstra et al.

(10) Patent No.: US 6,606,901 B1
(45) Date of Patent: Aug. 19, 2003

(54) PROCESS FOR DETERMINING THE ACIDITY OF A WASHING SOLUTION FOR FIBERS

(75) Inventors: Willem G. Haanstra, Westervoort (NL); Hendrikus J. M. Busschers, Enschede (NL)

(73) Assignee: Teijin Twaron B.V., Arnhem (NL)

( * ) Notice: Subject to any disclaimer, the term of this patent is extended or adjusted under 35 U.S.C. 154(b) by 0 days.

(21) Appl. No.: 10/070,135

(22) PCT Filed: Aug. 31, 2000

(86) PCT No.: PCT/EP00/08845
§ 371 (c)(1),
(2), (4) Date: Mar. 4, 2002

(87) PCT Pub. No.: WO01/18537
PCT Pub. Date: Mar. 15, 2001

(30) Foreign Application Priority Data

Sep. 2, 1999 (EP) .............................................. 99202845

(51) Int. Cl.$^7$ ................................................ G01N 11/00
(52) U.S. Cl. .................................................... 73/53.01
(58) Field of Search .......................... 702/81; 73/53.01, 73/53.03, 61.41; 264/178 R

(56) References Cited

U.S. PATENT DOCUMENTS

| | | | | |
|---|---|---|---|---|
| 3,780,577 A | * | 12/1973 | Brown | .................... 73/861.28 |
| 3,888,726 A | * | 6/1975 | Hultman | ...................... 162/49 |
| 4,918,979 A | | 4/1990 | Pearce et al. | |
| 4,996,160 A | | 2/1991 | Hausman Hazlitt et al. | |
| 5,760,297 A | * | 6/1998 | Weerstra | .................... 73/53.01 |

FOREIGN PATENT DOCUMENTS

| | | |
|---|---|---|
| DE | 195 33 927 A1 | 3/1997 |
| FR | 2 145 795 A | 2/1973 |
| GB | 950 198 A | 2/1964 |
| GB | 2 217 848 A | 11/1989 |

* cited by examiner

*Primary Examiner*—Hezron Williams
*Assistant Examiner*—Charles D Garber
(74) *Attorney, Agent, or Firm*—Oliff & Berridge, PLC

(57) ABSTRACT

The invention pertains to a process for determining the acidity of a washing solution for removing adhering acid or base from a fibre. The determination is carried out by using a combination of at least two different analytical methods, at least one of which is selected from the density, conductivity, ultrasonic sound, and refractive index measurements. The determination makes it possible to adjust the acidity of the washing solution in such a way that fibres with a minimum amount of adhering acid or base can be produced.

9 Claims, No Drawings

PROCESS FOR DETERMINING THE ACIDITY OF A WASHING SOLUTION FOR FIBERS

BACKGROUND OF INVENTION

1. Field of Invention

The invention pertains to a process for determining the acidity of a washing solution for removing adhering acid or base from a fibre.

2. Description of Related Art

There are different ways to produce fibres. The most widely used fibre-forming processes are melt spinning and solution spinning. In both processes, the polymer is extruded through the orifices of a spinneret. In melt spinning molten polymer is used, while in solution spinning use is made of a spinning dope solution comprising a dispersed or dissolved polymer. After the extrusion of the molten polymer or the spinning dope solution, different spinning techniques can be applied to produce the fibres.

Spinning dope solutions can be acidic. For example, a polymer comprising poly(p-phenylene terephthalamide) is usually dispersed in a sulfuric acid solution for the production of aramid fibres. After the solution has been extruded and a spinning technique applied, traces of the acidic solution often adhere to the produced fibres. These traces need to be removed in order to prevent hydrolytic degradation of the fibres, which occurs especially above 20° C.

Commonly, a washing solution is used to remove adhering acids or bases from a fibre. It is important to measure and adjust the acidity of the washing solution in such a way that fibres with a minimum amount of adhering acid or base can be produced. The acidity can be measured directly by using a titration method or a pH measurement. However, pH measurements are not preferred for accurate determination of the acidity because there is a necessity to calibrate the pH electrode very often and because the inaccuracy of the measurement increases as the pH-value deviates further from pH 6 to 8. Most commonly, the acidity of the washing solution is measured using a titration method, as described in M. Valcarcel et al., *Techniques and Instrumentation in Analytical Chemistry*, Vol. 9, Elsevier, Amsterdam, 1988. However, the information time of said titration method is relatively long. Therefore, it is very difficult or even impossible to adjust the acidity quickly enough to obtain fibres with a minimum amount of adhering acid or base. Another disadvantage of said method is the need to use reagents when carrying out a titration. Furthermore, a titration device used for measuring the acidity of a washing solution on-line requires relatively frequent maintenance.

SUMMARY OF THE INVENTION

The acidity of a washing solution can also be determined indirectly by using another analytical method such as a density, conductivity, ultrasonic sound or refractive index measurement. However, the results obtained carrying out one of these measurements in a washing solution are insufficient for accurate determination of the acidity when there are variable concentrations of salts or compounds present in the solution. For example, if sulfuric acid is used for the preparation of a spinning dope solution for the production of fibres, and traces of the solution still adhere to the produced fibres before washing, then variable concentrations of sodium sulfate will often be present in a washing solution for these fibres after interaction of the sulfuric acid with, for example, caustic soda.

It is accordingly the principal object of the present invention to provide a method for rapid and accurate determination of the acidity of a washing solution for the production of fibres with a minimum amount of adhering acid or base. Preferably, the method is applicable on-line. Furthermore, the device used for the determination preferably requires less maintenance than do the commercially available devices presently employed in the commonly used titration methods.

Surprisingly, a process has been found that permits rapid and accurate determination of the acidity of a washing solution for removing adhering acid or base from a fibre. The process is characterized in that the determination is carried out using a combination of at least two different analytical methods, at least one of which is selected from the density, conductivity, ultrasonic sound, and refractive index measurements. Rapid and accurate determination makes it possible to adjust the acidity of a washing solution in such a way that fibres with a minimum amount of adhering acid or base can be produced.

By fibres with a minimum amount of adhering acid or base is meant that the molar ratio of the $OH^-$ ions to the $H^+$ ions present in the medium adhering to said fibres is about 1, with the proviso that these ions are not chemically bound to the fibres. This ratio can be determined indirectly by analyzing the amount of counter-ions of the $OH^-$ and the $H^+$ ions in the medium, for example the amount of $Na^+$ ions when NaOH is used for washing the fibre and the amount of $SO_4^{2-}$ ions when the fibre is spun from a sulfuric acid solution. In this specific example a Na/S ratio can be determined by using X-ray diffraction spectroscopy (XRF). However, any other suitable analytical method may also be used.

DETAILED DESCRIPTION OF PREFERRED EMBODIMENTS

Preferably, the combination according to the invention comprises at least two analytical methods selected from the density, conductivity, ultrasonic sound and refractive index measurements. The analytical devices used for said measurements require less maintenance and are easier to calibrate than the commercially available devices presently employed in the commonly used titration methods. Furthermore, the devices used for these measurements are most practical when it comes to installation for measuring on-line.

Even more preferably, the combination according to the invention comprises a conductivity measurement or a density measurement, because such a combination enables highly accurate determination of the acidity of a washing solution for fibres. This is especially the case for a process according to the invention wherein the combination comprises at least : 1) a conductivity measurement and an ultrasonic sound measurement, 2) a conductivity measurement and a density measurement, or 3) a density measurement and an ultrasonic sound measurement. Most preferably, the combination comprises at least a conductivity measurement and an ultrasonic sound measurement, because the devices used for these measurements are easiest to clean and require the least maintenance. This is especially desirable when the measurements are carried out on-line.

The measurements "are carried out on-line" means that they are carried out continuously or at certain time intervals in a washing solution or any process stream consisting of this solution. Preferably, the measurements are carried out on-line automatically, for example controlled by an electronic and/or computer system. Even more preferably, said system is able to give signals or commands for correcting the acidity of the washing solution when necessary, thereby enabling the production of a fibre with a minimum amount of adhering acid or base.

The acidity of a washing solution for fibres can be determined by combining the results obtained by carrying out at least two analytical methods according to the invention. First, calibrations need to be carried out in order to determine the correlation of the results of each method with the acidity of the washing solution. Such a calibration is best performed by measuring on representative samples with different concentrations of salts or compounds, which are also -present in the washing solution for fibres of which the acidity needs to be determined, the different concentrations in the samples having been chosen according to an experimental design. An example of such an experimental design can be found in Table I of Example I. A calibration equation for each combination of analytical methods can be calculated from the results obtained by measuring in the samples, using a standard statistical technique, e.g. multiple linear regression or partial least squares, as described in H. Martens et al., *Multivariate calibration*, John Wiley and Sons, Chichester, 1989, or in D. L. Massart et al., *Chemometrics: A Textbook*, Elsevier, Amsterdam, 1987.

The process according to the invention can be used to remove adhering acid or base from any fibre. For example, the process can be applied to fibres produced using an acidic spinning dope solution comprising an aromatic polyamide, such as poly(p-phenylene terephthalamide), and sulfuric acid.

If a combination of analytical methods according to the invention comprising at least an ultrasonic sound measurement is used, then the propagation velocity of ultrasonic sound in a washing solution is measured using an ultrasonic device comprising an emitter and a receiver for ultrasonic sound. The device generates ultrasonic sound waves at the emitter, measures the time it takes before such a wave from the emitter passing through the solution arrives at the receiver, and calculates the propagation velocity as the distance between the emitter and the receiver divided by this time. Ultrasonic sound with a frequency of at least 50 kHz can be used for this measurement.

The propagation velocity (v) of ultrasonic sound in general depends on the density (d) and the adiabatic compressibility (c) of a solution according to the following equation:

$$v = \sqrt{\frac{1}{c*d}}$$

Consequently, if the density of the solution decreases, then the propagation velocity of ultrasonic sound in the solution increases. The density is dependent, int. al., on the temperature, the pressure, and the concentration of any compound or salt in the solution, such as sodium sulfate, sodium chloride, sodium hydroxide. Therefore, the propagation velocity of ultrasonic sound in a washing solution is not only dependent on the concentration of a compound or salt, but also on the temperature and the pressure in this solution. Preferably, the ultrasonic device used for measuring the propagation velocity of ultrasonic sound comprises a temperature sensor in order to enable a local adjustment of the temperature in the solution between the emitter and receiver.

The propagation velocity of ultrasonic sound in a washing solution is also slightly dependent on the flow of the solution in which the measurement takes place. Preferably, this propagation velocity is measured perpendicular to the flow direction.

If a combination of analytical methods according to the invention comprising at least a conductivity measurement, or a density measurement, or a refractive index measurement is used, then these measurements are carried out according to general conditions and instructions as described in F. McLennan and B. Kowalski., *Process Analytical Chemistry*, Glasgow, 1995.

The invention will be further illustrated with reference to the following examples.

EXAMPLE I

The samples characterized in Table I were prepared by adding the required amount of salt to aqueous solutions. The different concentrations of sodium hydroxide (NaOH), sodium sulfate ($Na_2SO_4$), and sodium carbonate ($Na_2CO_3$) in the samples were chosen according to a central composite design. The samples are representative of the composition of a washing solution for aramid fibres with adhering traces of sulfuric acid.

TABLE I

| Sample | NaOH (% by weight) | $Na_2CO_3$ (% by weight) | $Na_2SO_4$ (% by weight) |
|---|---|---|---|
| 1 | 0.66 | 0.070 | 1.60 |
| 2 | 1.34 | 0.070 | 1.60 |
| 3 | 1.01 | 0.020 | 1.60 |
| 4 | 1.00 | 0.120 | 1.60 |
| 5 | 1.00 | 0.070 | 0.09 |
| 6 | 1.00 | 0.070 | 3.11 |
| 7 | 0.80 | 0.041 | 0.70 |
| 8 | 1.20 | 0.040 | 0.71 |
| 9 | 0.80 | 0.100 | 0.70 |
| 10 | 1.20 | 0.100 | 0.70 |
| 11 | 0.80 | 0.040 | 2.50 |
| 12 | 1.21 | 0.040 | 2.50 |
| 13 | 0.79 | 0.102 | 2.51 |
| 14 | 1.19 | 0.100 | 2.50 |
| 15 | 1.00 | 0.072 | 1.61 |

Measurements were carried out on the above-mentioned samples using the analytical methods and devices specified below in Table II. The measurements were carried out at ambient pressure and room temperature. The density measurements were corrected to 25° C. The results of the measurements are presented in Table III.

TABLE II

| Analytical method | Abbreviation | Device |
|---|---|---|
| Density measurement | (d) | Kyoto DA 310M |
| Conductivity measurement | (c) | Yokogawa ISC40G-PG-T1-05 (inductive type of measurement) |
| Ultrasonic sound measurement | (v) | LiquiSonic 30 (SensoTech) |
| Refractive Index measurement | (ri) | Krüss AR-8 |

TABLE III

| Sample | Conductivity (mS) | Density (g/ml) | Propagation velocity of ultrasonic sound (m/s) | Refractive Index |
|---|---|---|---|---|
| 1 | 46.20 | 1.019385 | 1519.11 | 1.3376 |
| 2 | 75.29 | 1.026820 | 1535.77 | 1.3394 |

TABLE III-continued

| Sample | Conductivity (mS) | Density (g/ml) | Propagation velocity of ultrasonic sound (m/s) | Refractive Index |
|---|---|---|---|---|
| 3 | 60.02 | 1.022725 | 1526.60 | 1.3384 |
| 4 | 60.75 | 1.023645 | 1528.26 | 1.3384 |
| 5 | 49.20 | 1.009595 | 1509.88 | 1.3362 |
| 6 | 70.00 | 1.036765 | 1544.52 | 1.3405 |
| 7 | 44.94 | 1.012645 | 1511.48 | 1.3365 |
| 8 | 62.19 | 1.016990 | 1521.74 | 1.3374 |
| 9 | 45.97 | 1.013190 | 1512.39 | 1.3365 |
| 10 | 63.21 | 1.017640 | 1522.58 | 1.3376 |
| 11 | 57.93 | 1.028780 | 1532.10 | 1.3389 |
| 12 | 74.32 | 1.033185 | 1542.39 | 1.3401 |
| 13 | 58.56 | 1.029385 | 1533.26 | 1.3394 |
| 14 | 74.08 | 1.033675 | 1543.10 | 1.3405 |
| 15 | 60.05 | 1.023195 | 1527.50 | 1.3384 |

The correlation coefficients for the NaOH concentration presented in Table IV were determined from these results for each analytical method according to standard statistical methods.

TABLE IV

| Analytical method | Correlation coefficient for the NaOH concentration |
|---|---|
| Conductivity measurement | 0.806 |
| Density measurement | 0.258 |
| Ultrasonic sound measurement | 0.433 |
| Refractive Index measurement | 0.367 |

It was concluded from Table IV that the results for each analytical method as such do not show a good correlation with the sodium hydroxide concentration. Therefore, it is not possible to determine accurately the acidity of a washing solution comprising variable concentrations of compounds or salts when only one of the analytical methods is used.

EXAMPLE II

The results of two different analytical methods in Table III were combined in order to determine the correlation of these combined results with the sodium hydroxide concentration.

The predicted error (expressed as the standard deviation of the difference between prediction and reference value) in the NaOH concentration was determined for each combination of analytical methods as presented in Table V, using multivariate mathematical techniques, e.g. partial least squares or multiple linear regression.

It was concluded from Table V that especially the combined results of the following combinations of analytical methods (for abbreviations, see Table II) show a good correlation with the NaOH concentration in this example: (c)+(d), (c)+(v), (c)+(ri), and (d)+(v). The correlation of these combined results with the NaOH concentration is far better than the correlation of the results of just one analytical method with the NaOH concentration, as described in Example I.

What is claimed is:

1. A process for producing fibers having a minimum amount of adhering acid or base comprising:
   extruding a fiber-forming polymer through the orifices of a spinneret to form a fiber, preparing a washing solution, including
   determining an acidity of the washing solution by carrying out a combination of at least two different analytical methods, at least one of which is selected from the group consisting of density measurements, conductivity measurements, ultrasonic sound measurements, and refractive index measurements, and
   correcting the acidity of the washing solution to a necessary acidity value following the determining step if the acidity determined is different from the necessary acidity value, thereby deriving the washing solution having the acidity value necessary for yielding the fiber having a minimum amount of adhering acid or base following washing of the fiber with the washing solution, and
   washing the fiber with the washing solution to remove adhering acid or base from the fiber.

2. The process according to claim 1, wherein at least another of the analytical methods of the combination is selected from the group consisting of density measurements, conductivity measurements, ultrasonic sound measurements, and refractive index measurements.

3. The process according to claim 1, wherein at least one of the analytical methods of the combination is an ultrasonic sound measurement.

4. The process according to claim 1, wherein at least one of the analytical methods of the combination is a conductivity measurement or a density measurement.

5. The process according to claim 3, wherein at least another of the analytical methods of the combination is a conductivity measurement.

6. The process according to claim 1, wherein the combination of analytical methods is a conductivity measurement and a density measurement.

7. The process according to claim 3, wherein at least another of the analytical methods of the combination is a density measurement.

8. The process according to claim 1, wherein the analytical methods are carried out on-line.

TABLE V

| Conductivity measurement | Density measurement | Ultrasonic sound measurement | Refractive Index measurement | Predicted error in NaOH concentration (% by weight) | Correlation coefficient |
|---|---|---|---|---|---|
| + | + | | | 0.015 | 0.997 |
| + | | + | | 0.016 | 0.997 |
| + | | | + | 0.024 | 0.993 |
| | + | + | | 0.019 | 0.996 |
| | + | | + | 0.119 | 0.803 |
| | | + | + | 0.139 | 0.718 |

9. The process according to claim 1, wherein the determining further comprises carrying out a calibration for determining a correlation of results for each analytical method of the combination of analytical methods with the acidity of the washing solution by measuring representative samples having different concentrations of salts or compounds and calculating a calibration equation for the combination of analytical methods.

* * * * *